(12) United States Patent
Carter

(10) Patent No.: US 6,718,980 B2
(45) Date of Patent: Apr. 13, 2004

(54) TREATMENT OF CARBON MONOXIDE POISONING

(75) Inventor: Stephen A. Carter, Calgary (CA)

(73) Assignee: Veritek NGV (CA)

( * ) Notice: Subject to any disclaimer, the term of this patent is extended or adjusted under 35 U.S.C. 154(b) by 0 days.

(21) Appl. No.: 10/016,666

(22) Filed: Oct. 26, 2001

(65) Prior Publication Data

US 2002/0112722 A1 Aug. 22, 2002

Related U.S. Application Data

(63) Continuation of application No. PCT/CA00/00481, filed on Apr. 26, 2000.

(30) Foreign Application Priority Data

Apr. 26, 1999  (CA) ............................................. 2269890

(51) Int. Cl.[7] ................................................ A62B 9/02
(52) U.S. Cl. ........................... 128/205.24; 128/203.12; 128/205.11; 128/207.12; 128/207.17
(58) Field of Search ....................... 128/203.12, 203.16, 128/203.18, 203.22, 203.23, 203.24, 203.25, 205.11, 205.24, 207.12, 207.17

(56) References Cited

U.S. PATENT DOCUMENTS

| | | | |
|---|---|---|---|
| 3,717,177 A | * | 2/1973 | Glesmann .................... 137/607 |
| 3,875,968 A | * | 4/1975 | Olofsson et al. .......... 137/636.1 |
| 3,910,222 A | | 10/1975 | Metivier ....................... 116/70 |
| 4,054,133 A | | 10/1977 | Myers ...................... 128/142.2 |
| 4,148,311 A | * | 4/1979 | London et al. .......... 128/204.26 |
| 4,244,396 A | * | 1/1981 | Friedland et al. ........ 137/487.5 |
| 4,449,524 A | * | 5/1984 | Gray ...................... 128/202.27 |
| 4,465,089 A | * | 8/1984 | Inhofer ........................ 137/101 |
| 4,535,797 A | * | 8/1985 | Rosaen .................... 137/87.03 |
| 4,546,794 A | * | 10/1985 | Ball ........................ 137/599.03 |
| 4,549,563 A | | 10/1985 | Monnier ..................... 137/100 |
| 4,554,916 A | | 11/1985 | Watt ....................... 128/203.12 |
| 4,648,395 A | * | 3/1987 | Sato et al. ............. 128/204.23 |
| 4,807,615 A | * | 2/1989 | Nakagawa et al. ..... 128/203.12 |
| 4,827,965 A | * | 5/1989 | Wates .......................... 137/88 |
| 4,924,900 A | * | 5/1990 | Taube et al. ................ 137/101 |
| 5,241,987 A | * | 9/1993 | Ohmi et al. ................ 137/597 |
| 5,470,511 A | * | 11/1995 | Laybourne et al. ........... 261/55 |
| 5,722,392 A | * | 3/1998 | Skimming et al. ..... 128/203.12 |
| 5,887,611 A | | 3/1999 | Lampotang et al. .......... 137/93 |
| 6,041,777 A | * | 3/2000 | Faithfull et al. ....... 128/200.24 |

* cited by examiner

Primary Examiner—Weilun Lo
Assistant Examiner—Michael G. Mendoza
(74) Attorney, Agent, or Firm—Norris McLaughlin & Marcus, P.A.

(57) ABSTRACT

An improved therapy for both clearing the blood of unwanted carbon monoxide and anaesthetic chemicals and for rapidly re-oxygenating blood suffering from carbon monoxide poisoning or smoke inhalation. It also includes a therapy delivery device for carbon dioxide and oxygen metering and mixing apparatus for gases under pressure particularly for respirators and medical devices which has a plurality of compressed gas supply lines which are connected to a mixing device for delivery into a demand regulator (respirator or face mask). It includes a gas selection device, an automatic shut off of the carbon dioxide, a purging system, metering of the gases and a mixing chamber to promote a homogeneous mixture of gases and sized for field use by emergency care operators. The therapy is a mixture of carbon dioxide and oxygen for promoting the rapid oxygenation of the patient's blood supply for cases of carbon monoxide poisoning, smoke inhalation or other cases where the blood oxygen level is low.

26 Claims, 5 Drawing Sheets

TREATMENT OF CARBON MONOXIDE POISONING

CROSS REFERENCE TO RELATED APPLICATIONS

This application is a continuation of International Application PCT/CA00/00481, filed Apr. 26, 2000, which is hereby incorporated herein by reference in its entirety.

FIELD OF THE INVENTION

This invention relates to a therapy for clearing the blood of unwanted carbon monoxide and anaesthetic chemicals and for rapidly re-oxygenating that has had it's oxygen level depleted by environmental conditions i.e. carbon monoxide poisoning or smoke inhalation. The invention includes the means of delivering the therapy in a convenient manner whether given in-situ, in an ambulance or other emergency response vehicle, or at the hospital or other care facility, and whether administered by medical professionals or paramedical personnel. The device relates in general to pneumatic/mechanical control of respirator gas supply control devices and in particular to gas selection, automatic shut off of the carbon dioxide, purging, metering and mixing of the therapeutic gases.

BACKGROUND OF THE INVENTION

Carbon monoxide (CO) is a tasteless, colorless, odourless gas. Thus it is undetectable by potential victims. The blood prefers CO to oxygen by a ratio of 200:1. As a result, relatively small amounts of CO in the air can cause CO poisoning. CO attaches to blood forming carboxyhemoglobin, thus starving the brain and other organs and tissues for oxygen ($O_2$). Carbon monoxide poisoning occurs when carboxyhemoglobin levels are high enough to impair cellular functions. Symptoms of carbon monoxide poisoning include drowsiness, nausea and possibly death. The CO poisoning rate is significant, with over 70,000 hospital visits and 10,000 deaths per year in the U.S.

The cellular oxygen starvation from CO poisoning can cause death, or long-term, non-reversible health problems (i.e. to the brain, heart or neurological system). If a CO poisoning victim does not die, the average body will clear carboxyhemoglobin at the following typical rates:
Spontaneous breathing–cleansing half-life =220 minutes; Breathing pure $O_2$=40 minutes; Hyperbaric chamber=20 minutes.

While the best current therapy is placing the patient in a hyperbaric chamber, these chambers are usually unavailable (only about 700 exist world-wide) and are rarely used. Typically these chambers require a "warm-up" time of 2 hours, which largely negates their theoretical usefulness. That is, significant permanent damage may have already occurred before the treatment can be commenced.

The current therapy of choice is to administer pure $O_2$. As suggested above, pure $O_2$ would require approximately 2 hours to clear 87.5% of the CO from the bloodstream (e.g. 40 minutes=50% of CO is eliminated; 80 minutes=25%; 120 minutes=12.5%). Breathing pure $O_2$ has an unfortunate side effect; it lowers the respiratory rate and reduces the exchange of gases in the lungs, thereby prolonging the tissue starvation period. Accordingly, there is a need for a device that would overcome these disadvantages.

Typical respirator gas supply control devices, particularly those used for mixing gases under pressure and feed a delivery line of a respirator, or medical device, are too large and bulky to be used in situ or in emergency vehicles. They also require the operation of a skilled, medical practitioner to properly administer. A complete system that can be used by emergency and paramedical should have a gas selection device, an automatic shut off of the carbon monoxide a purging system, metering of the gases and a mixing chamber to promote a homogeneous mixture of gases and sized for in-situ or vehicle as well as hospital emergency room use. It should be able to use a whole range of different gas storage systems for input and demand regulators and facemasks as output. It can not rely on electrical control of the gas flow and mixing as power demand for both in situ or emergency vehicle applications is already greater than is reasonable to expect. Also electrical power at fire and other emergency sites is problematical to provide and higher priority uses get first use of this power. Finally battery power is not acceptable as the system must operate every time demanded regardless of the interval between demand and maintenance of batteries is a low priority item for emergency care providers.

For example, U.S. Pat. 3,441,041 allows for either atmospheric or compressed air to be used for a breathing apparatus but the mixture device is not easily portable, and requires adjustment by a trained individual when dealing with a patient to determine if the by-pass should be opened or closed and to adjust the compressed air flow based on respiration demands and the state of the patient's health.

U.S. Pat. 4,535,797 discloses a device that uses flow to keep the by-pass open and the by-pass is required to open the gas flow valve for the first time. Should the $CO_2$ supply fail, the $O_2$ supply will shut and the patient's therapy is terminated.

U.S. Pat. 4,549,563 maintains a constant ratio between two gases, G1 and G2, by keeping the pressure of both gases P1 and P2 constant and keeps P1 constant at a set rate of flow through the use of a pressure limiter.

The device disclosed in U.S. Pat. 4,549,563 does not provide for automatic shut off of the $CO_2$ gas stream should the $O_2$ stream become clogged. This shortcoming would expose the patient to an asphixyant and would not revert to the previously accepted therapy. In U.S. Pat. 4,549,563 the practitioner operates the flush system described in case the patient requires pure $O_2$ instead of the gas mixer. Such facemasks are commercially available and are not shown in the drawings. Also the system in 4,549,563 has no means of purging, which would mean that the second patient would face an incorrect mixture or if the system selection was changed, for example from $O_2$ to $CO_2$ then the patient would have to inhale the incorrect mixture prior to receiving the correct therapeutic gases.

U.S. Pat. 4,313,436 mixes $O_2$ and other medical gases for patients. It requires electronic sensing to determine if the gas mixture is correct and if not then causes a pressure pulse to close the by-pass thereby allowing only pure $O_2$ to enter the facemask. The use of electronics that have a large demand for power, i.e. 4 sensors and an automatic controller, are not feasible for in-situ on in vehicle use where power demand is already quite high and the most frequent operational problem is dead batteries due to limited maintenance time. Also this device has up to 5 separate valves that need to be adjusted by the medical practitioner to ensure the patient is receiving the proper gas mixture depending on his state. This degree of adjustment is inimical to the use by paramedical and emergency personnel. The system in 4,313,436 lacks a means of purging and only has two selection options, no mixture or mixture. Since there is no intermediary stage the operator is not prompted to purge the system.

U.S. Pat. 4,827,965 uses a venturi nozzle to simultaneously meter and mix the two gases in proper proportions.

This scheme means that pressure of the two gases varies over the flow demand regime and that the charge may be stratified. Finally the system in 4,827,965 does not have a means to shut off the $CO_2$ mixture thus potentially exposing the patient to an asphixyant. Nor does it allow selection of different options (i.e. $O_2$ only, off, mix or off). Nor does it offer a means of purging the system except by drawing off the first amount of improper mixture.

Under U.S. Pat. 5,727,545, one embodiment requires electronic sensing of two temperatures and a pressure to control the action of four flow regulators. In a second embodiment, it requires electronic sensing of two temperatures and a pressure to control the action of two flow regulators. The by-pass is driven electronically so that any failure of the electrical system would endanger the patient's life. Metering and mixing are all electronic and it has no purging means. The use of electronics that have a large demand for power are not feasible for in-situ on in vehicle use where power demand is already quite high and the most frequent operational problem is dead batteries due to limited maintenance time.

U.S. Pat. 4,508,143 discloses the use of a cam actuator to open a valve. It opens two poppet valves either automatically or manually. 4,508,143 has no other features that could deliver or control the therapeutic gas delivery.

SUMMARY OF THE INVENTION

The invention provides a therapy clearing the blood of unwanted carbon monoxide and anaesthetic chemicals and for rapidly re-oxygenating that has had its oxygen level depleted by environmental conditions, i.e. carbon monoxide poisoning or smoke inhalation. The invention includes delivering the therapy in a convenient manner in situ, in an ambulance or other emergency response vehicle, or at the hospital or other care facility. It may be administered by medical professionals or paramedical personnel. The device relates in general to respirator gas supply control devices and in particular to gas selection, automatic shut off of the carbon monoxide, purging, metering and mixing of the therapeutic gases.

It is a great improvement on the current therapy, using pure $O_2$, in that it is more rapidly clears carboxyhemoglobin from the patient's blood stream. Also it does not lower the respiratory rate or reduce the exchange of gases in the lungs, thereby prolonging the tissue starvation period. In fact the body's autonomous responses in the presence of a $CO_2$ rich environment is to increase the rate of respiration (panting) thus further decreasing the tissue starvation period. While the method of invention and the use of a hyperbaric chamber are both effective, a hyperbaric chamber is impractical for in situ and vehicle applications due to their size, cost, long warm up time and requirement for trained medical practitioner for operation.

Cellular oxygen starvation from CO poisoning, or smoke inhalation, can cause death, or long-term, non-reversible health problems (i.e. to the brain, heart or neurological system). In the United States alone there are 70,000 hospital visits and 10,000 deaths per year due to CO poisoning. Thus a new therapy that radically improves the outcomes of patients exposed to CO poisoning is needed.

The invention also includes a device for delivering the improved therapy for in situ, in vehicles (i.e. ambulance or fire truck) and institutional (i.e. hospital) locations. It avoids the above-described shortcomings for example where the system requires electric power to properly operate, making it impractical for most emergency applications. It avoids the requirement for a trained medical practitioner to properly operate and adjust the system while monitoring the patient's state of health. It avoids the requirement to add other required functions to the system with external components.

The invention optionally includes all the functions required of an integrated system: selection of therapy; automatic shut-off of $CO_2$; (i.e. automatic use of current therapy pure $O_2$) or in case of $O_2$ interruption automatic use of atmospheric air; precision metering of both gases; excellent mixing of both gases; and system purging. One embodiment allows for the use of the use of any $O_2$ and $C O_2$ supply to accommodate institutional demands (i.e. hospitals). The first embodiment includes a pneumatic control device. The second embodiment includes its own portable $CO_2$ supply to allow use with existing portable $O_2$ supplies found in all emergency response vehicles. The second embodiment contains all items required for the therapy except the external $O_2$ supply.

A cam actuator is used to select the choice of gas that the patient receives and is a four-position, rotary, manual switch. It can either be $O_2$, off, $O_2/CO_2$, off. The two intermediary "off" positions allow for the patient to breathe atmospheric air and are a reminder to the operator to purge the system prior to moving to the next selection position.

Should one of the source gas pressures become too low to maintain a proper therapeutic gas mixture then the $CO_2$ flow would be halted by the shut-off valve. A $CO_2$ shutoff is operated by differential pressure between the $O_2$ and the $CO_2$ gas mixture; failing a proper supply of $O_2$, the $CO_2$ shut-off closes so that only atmospheric air or $O_2$ can be inhaled. This is acceptable as the system reverts to the previously acceptable therapy. In case of $O_2$ flow interruption the $CO_2$ flow stops and automatically the patient inhales atmospheric air through the facemask by-pass valve.

The pressure of one gas G 1 ($O_2$) maintains the flow of the other gas G2 ($CO_2$), since PI keeps the G2 flow passage open. Metering is done separately for each gas and is automatic and based on sonic flow of the gases, but accepts sub-sonic flow for either or both gases. Metering keeps the flow proportional regardless of outlet demand, and mixing is done in a separate chamber where the gas path maximises the chance of a homogeneous mixture.

The invention relates to an apparatus and method for clearing the blood of unwanted carbon monoxide and/or anaesthetic chemicals and for rapidly re-oxygenating that has had it's oxygen level depleted, for example by environmental conditions i.e. carbon monoxide poisoning or smoke inhalation. The therapy includes respiration by the patient of a mixture of $CO_2$ and $O_2$. The apparatus for treating preferably involves administering to the subject oxygen from a source of oxygen and carbon dioxide from a source of carbon dioxide, comprises:

an oxygen conduit defining an oxygen inlet and an oxygen outlet, the oxygen inlet adapted for fluid communication with the source of oxygen;

a carbon dioxide conduit defining a carbon dioxide inlet and a carbon dioxide outlet, the carbon dioxide inlet adapted for fluid communication with the source of carbon dioxide;

a means for combining the oxygen and the carbon dioxide, the means downstream from the oxygen outlet and the carbon dioxide outlet; and a means for administering the combined oxygen and carbon dioxide to the subject.

The invention also includes a portable kit including the apparatus. The invention also includes a method for removing carbon monoxide and/or anaesthetic chemicals from blood and for rapidly re-oxygenating that has had it's oxygen level depleted, including administering to a subject an effective amount of combined oxygen and carbon dioxide from the apparatus. The invention also includes the use of the apparatus for removing carbon monoxide and/or anaesthetic chemicals from blood and for rapidly re-oxygenating that has had it's oxygen level depleted.

Oxygen and carbon dioxide therapy using the apparatus and methods of the invention can produce a clearing half-life of about 20 minutes.

The invention relates to an improved therapy for clearing the blood of unwanted carbon monoxide and anaesthetic chemicals and for rapidly re-oxygenating that has had it's oxygen level depleted by environmental conditions i.e. carbon monoxide poisoning or smoke inhalation. The therapy includes respiration by the patient of a mixture of $CO_2$ and $O_2$. The invention includes an apparatus and method for delivering the improved therapy in a convenient manner whether given in-situ, in an ambulance or other emergency response vehicle, or at the hospital or other care facility, and whether administered by medical professionals or paramedical personnel, and does not require the use of electrical power. In one embodiment, the apparatus acts as a pneumatic control device for the therapeutic gas mixture and where $O_2$ and $CO_2$ are stored. Preferably, pressure is regulated externally, an external buffer volume is stored externally and/or the demand regulator and facemask are connected to the equipment.

The invention also includes a method and apparatus for delivering the improved therapy, in the second embodiment, where all necessary functions are delivery of the therapeutic gas mixture is self-contained, with the sole exception of the $O_2$ supply.

The invention also includes a control system, in the first embodiment, which preferably includes: supplied gas shut-off valves; therapy selector switch; automatic shut-off valve for $CO_2$ supply to avoid asphyxiating the patient; separate $CO_2$ and $O_2$ metering valves; a common gas mixing chamber, outlet ports to the buffer volume; outlet ports to the demand regulator/facemask; a means to purge the system and the buffer volume of previous gas mixtures prior to each new use. This system requires external connections to pressurised $CO_2$ and $O_2$, a buffer volume and the demand regulator/facemask to operate.

The invention also includes a portable apparatus and method of delivering the improved therapy, for emergency personnel and first aid care givers at the emergency site, in the second embodiment, which includes: pressure regulation of supplied $O_2$; $CO_2$ cylinder; pressure regulation of supplied $CO_2$; $CO_2$ and $O_2$ gas shut-off valves; therapy selector switch; automatic shut-off valve for $CO_2$ supply to avoid asphyxiating the patient; separate $CO_2$ and $O_2$ metering valves; a common gas mixing chamber; a buffer volume; a demand regulator, hose and facemask; a means to purge the system and the buffer volume of previous gas mixtures prior to each new use. This embodiment only requires connection to an outside, readily available source of pressurised $O_2$ to operate. The invention also includes alternate methods of providing a suitable gas metering orifice. The invention also includes a member to filter either or both of the therapeutic gases prior to metering.

The invention also relates to a gas metering and mixing apparatus for gases under pressure, particularly for respirators and medical devices, comprising a plurality of gas meters, a gas mixer device, a plurality of compressed gas supply lines connected to said gas meters, a plurality of mixed gas delivery lines extending out of said gas mixer device for the discharge of a mixture of gases from said compressed gas supply lines from said gas meters and from said gas mixer device to a demand regulator, hose and facemask and to a buffer storage volume, and a means of selecting which gases, $O_2$, mixture or none, are sourced to said metering and mixing device and at least an automatic shutoff valve for one of the therapeutic gases, $CO_2$, which could in excess cause patient asphyxiation without said shut-off valve performing its function and with a means of purging the system including the buffer volume of mixed gases (or $O_2$ as appropriate). The automatic shut-off valve preferably includes means of adjusting said valve to vary the pressure in which it opens. The invention also includes a gas metering and mixing apparatus, wherein said metering can be adjusted to vary the proportions of the two different therapeutic gases. The apparatus preferably includes the use of sonic nozzles to meter said therapeutic gases. The invention also includes alternate devices for metering said therapeutic gases. The gas metering and mixing apparatus includes the ability to add filtration to the system as a means of protecting the sonic nozzles. The invention also includes a gas metering and mixing apparatus which includes the ability to add filtration to the system to protect the alternate metering means.

The invention includes an apparatus for treating carbon monoxide poisoning in a subject by administering to the subject oxygen from a source of oxygen and carbon dioxide from a source of carbon dioxide, comprising:
  an oxygen conduit defining an oxygen inlet and an oxygen outlet, the oxygen inlet adapted for fluid communication with the source of oxygen;
  a carbon dioxide conduit defining a carbon dioxide inlet and a carbon dioxide outlet, the carbon dioxide inlet adapted for fluid communication with the source of carbon dioxide;
  a means for combining the oxygen and the carbon dioxide, the means downstream from the oxygen outlet and the carbon dioxide outlet; and
  a means for administering the combined oxygen and carbon dioxide to the subject.

In a variation, apparatus comprises a gas control means associated with the apparatus for controlling the pressure, flow rate and the ratio of the combined oxygen and carbon dioxide. The gas control means optionally comprises an oxygen regulator for controlling oxygen pressure and a carbon dioxide regulator for controlling carbon dioxide pressure, the oxygen regulator located between the oxygen source and the combining means and the carbon dioxide regulator located between the carbon dioxide source and the combining means. The regulators also control nominal flow rate of the oxygen and carbon dioxide.

In a variation, the control means further comprises an oxygen sonic nozzle downstream of the oxygen regulator and a carbon dioxide sonic nozzle downstream of the carbon dioxide regulator, the nozzles dispensing the oxygen and the carbon dioxide. The nozzles dispense the oxygen and the carbon dioxide according to a predetermined flow rate. The apparatus preferably also comprises a means for reducing the flow of carbon dioxide when the percentage of carbon dioxide in the combined carbon dioxide and oxygen exceeds about 6.5% by volume. In another embodiment, the reducing means prevents the flow of carbon dioxide.

The invention also includes a variation where the means for reducing the flow of carbon dioxide comprises a differential pressure sensor downstream of the carbon dioxide source and/or the oxygen source.

Another variation involves the reducing means being located proximate to the conduits and in fluid communication with the oxygen and the carbon dioxide sources.

In another variation, the reducing means of the apparatus comprises: a shutoff member located proximate to the carbon dioxide conduit having an on position in which the shutoff member permits the carbon dioxide to communicate from the carbon dioxide source to the combining means and an off position in which the shutoff member prevents the carbon dioxide from communicating from the carbon dioxide source to the combining means; an actuating means for actuating the shutoff member from the on position to the off position when the percentage of carbon dioxide in the combined carbon dioxide and oxygen exceeds about 6.5% by volume, the actuating means operably connected to the shutoff member and responsive to differential pressure in the oxygen conduit and the carbon dioxide conduit. Optionally, the actuating means comprises:

a piston means in fluid communication with the oxygen conduit, the piston means located proximate to the oxygen conduit and including a first position in which the piston means is biased away from the oxygen conduit and actuates the shutoff member to the on position and a second position in which it is biased towards the oxygen conduit and actuates the shutoff member to the off position;

a biasing means for urging the piston toward the second position;

the piston means normally biased by oxygen toward the first position against the force of the biasing means, the piston means being urged toward the second position by the biasing means when oxygen pressure decreases in the oxygen conduit.

According to another aspect of the invention, the combining means comprises a mixing chamber.

In another variation, the administering means of the apparatus comprises a face-mask including a conduit in fluid communication with the combining means, the face-mask adapted for placement over the face of the subject. The face-mask optionally comprises a pressure regulator.

The invention also includes the variation where the apparatus further comprises a buffer in fluid communication with the combining means, the buffer including combined oxygen and carbon dioxide.

In another variation, the administering means is capable of administering the combined oxygen and carbon dioxide to the subject in an amount effective to increase the breathing rate of the subject. The carbon dioxide is about 3.5 to 6.5 percent by volume of the combined oxygen and carbon dioxide.

According to another aspect of the invention, the combined carbon dioxide and oxygen are in a ratio of about 19:1 by volume.

In a variation, the combined carbon dioxide and oxygen have a pressure of about 1 atm to 20 psig.

The invention also includes the variation where the oxygen conduit and the carbon dioxide conduits are connected to a tubular housing and extend into the housing.

In another variation, the conduits of the apparatus are defined by the housing, and are integrally defined by the housing.

In a variation the apparatus is portable. Portable means that the apparatus can fit inside an emergency vehicle and is practical for use in an emergency situation (for example, it can preferably be carried by a person). It further comprises optionally a carbon dioxide tank capable of connection to the carbon dioxide conduit. The apparatus is preferably capable of fitting in a briefcase. The subject is a mammal, preferably a human. The apparatus is preferably operable without electric power. It is optionally pneumatically powered.

The invention may also include a selector means or device to control the flow of carbon dioxide and oxygen. In one embodiment, the selector means may include a rotary selector 40. The invention may also include a purging means or device, such as the valve 140 and port 160 for purging carbon dioxide and oxygen.

Another embodiment of the invention relates to a portable kit for treating carbon monoxide poisoning, comprising the apparatus of the invention.

This invention also includes a method of treating carbon monoxide poisoning, comprising administering to a subject an effective amount of combined oxygen and carbon dioxide from the apparatus disclosed. The invention also includes the use of an apparatus of the invention for treatment of carbon monoxide poisoning.

The invention includes an apparatus for treating carbon monoxide poisoning in a subject by administering to the subject oxygen from a source of oxygen and carbon dioxide from a source of carbon dioxide, comprising:

an oxygen conduit defining an oxygen inlet and an oxygen outlet, the oxygen inlet adapted for fluid communication with the source of oxygen;

a carbon dioxide conduit defining a carbon dioxide inlet and a carbon dioxide outlet, the carbon dioxide inlet adapted for fluid communication with the source of carbon dioxide;

a device for combining the oxygen and the carbon dioxide, the device downstream from the oxygen outlet and the carbon dioxide outlet; and a device for administering the combined oxygen and carbon dioxide to the subject.

The apparatus optionally further comprises a gas control device associated with the apparatus for controlling the pressure, flow rate and the ratio of the combined oxygen and carbon dioxide.

The control device optionally further comprises an oxygen sonic nozzle downstream of the oxygen regulator and a carbon dioxide sonic nozzle downstream of the carbon dioxide regulator, the nozzles dispensing the oxygen and the carbon dioxide. The apparatus optionally further comprises a device for reducing the flow of carbon dioxide when the percentage of carbon dioxide in the combined carbon dioxide and oxygen exceeds about 6.5% by volume. The reducing device may comprise:

a shutoff member located proximate to the carbon dioxide conduit having an on position in which the shutoff member permits the carbon dioxide to communicate from the carbon dioxide source to the combining device and an off position in which the shutoff member prevents the carbon dioxide from communicating from the carbon dioxide source to the combining device;

an actuating device for actuating the shutoff member from the on position to the off position when the percentage of carbon dioxide in the combined carbon dioxide and oxygen exceeds about 6.5% by volume, the actuating device operably connected to the shutoff member and responsive to differential pressure in the oxygen conduit and the carbon dioxide conduit. The actuating device optionally comprises:

a piston device in fluid communication with the oxygen conduit, the piston device located proximate to the oxygen conduit and including a first position in which the piston device is biased away from the oxygen conduit and actuates the shutoff member to the on position and a second position in which it is biased towards the oxygen conduit and actuates the shutoff member to the off position;

a biasing device for urging the piston toward the second position;

the piston device normally biased by oxygen toward the first position against the force of the biasing device, the piston device being urged toward the second position by the biasing device when oxygen pressure decreases in the oxygen conduit. The device described 20 above may include various means, as described below.

BRIEF DESCRIPTION OF THE DRAWINGS

Embodiments of the invention will be described by way of example and with reference to the drawings in which.

DETAILED DESCRIPTION OF THE PREFERRED EMBODIMENTS

The invention comprises a pneumatic control assembly for metering and mixing $O_2$ and $CO_2$ in prescribed proportions. The system would preferably operate sonically, with sonic nozzle orifice sizes and pressures adjusted so that the gases are delivered in a 95% to 5% ratio by volume (see Marks Standard Handbook for Mechanical Engineers 9th Edition 1987; John B. Heywood, Internal Combustion Engine Fundamentals, McGraw Hill 1988). However, other ratios could readily be used: typically a useful range for carbon monoxide is from about 3.5 to 6.5 percent of the combined volume. The control system can be manually selected to deliver pure oxygen, the $O_2$—$CO_2$ mixture, or in two "pause" positions, no gases. A manual valve would preferably allow system purging by venting all contained gases to atmosphere. When operating, the system preferably monitors the $O_2$ and $CO_2$ input pressures. Should the two pressures become significantly different the system would automatically stop the $CO_2$ flow. This feature is desirable because high concentration or pure $CO_2$ delivery would cause asphyxiation.

The invention relates to an apparatus for treating carbon monoxide poisoning in a subject by administering to the subject oxygen from a source of oxygen and carbon dioxide from a source of carbon dioxide, comprising:

an oxygen conduit defining an oxygen inlet and an oxygen outlet, the oxygen inlet adapted for fluid communication with the source of oxygen;

a carbon dioxide conduit defining a carbon dioxide inlet and a carbon dioxide outlet, the carbon dioxide inlet adapted for fluid communication with the source of carbon dioxide;

a means for combining the oxygen and the carbon dioxide, the means downstream from the oxygen outlet and the carbon dioxide outlet; and a means for administering the combined oxygen and carbon dioxide to the subject.

Figure 2:
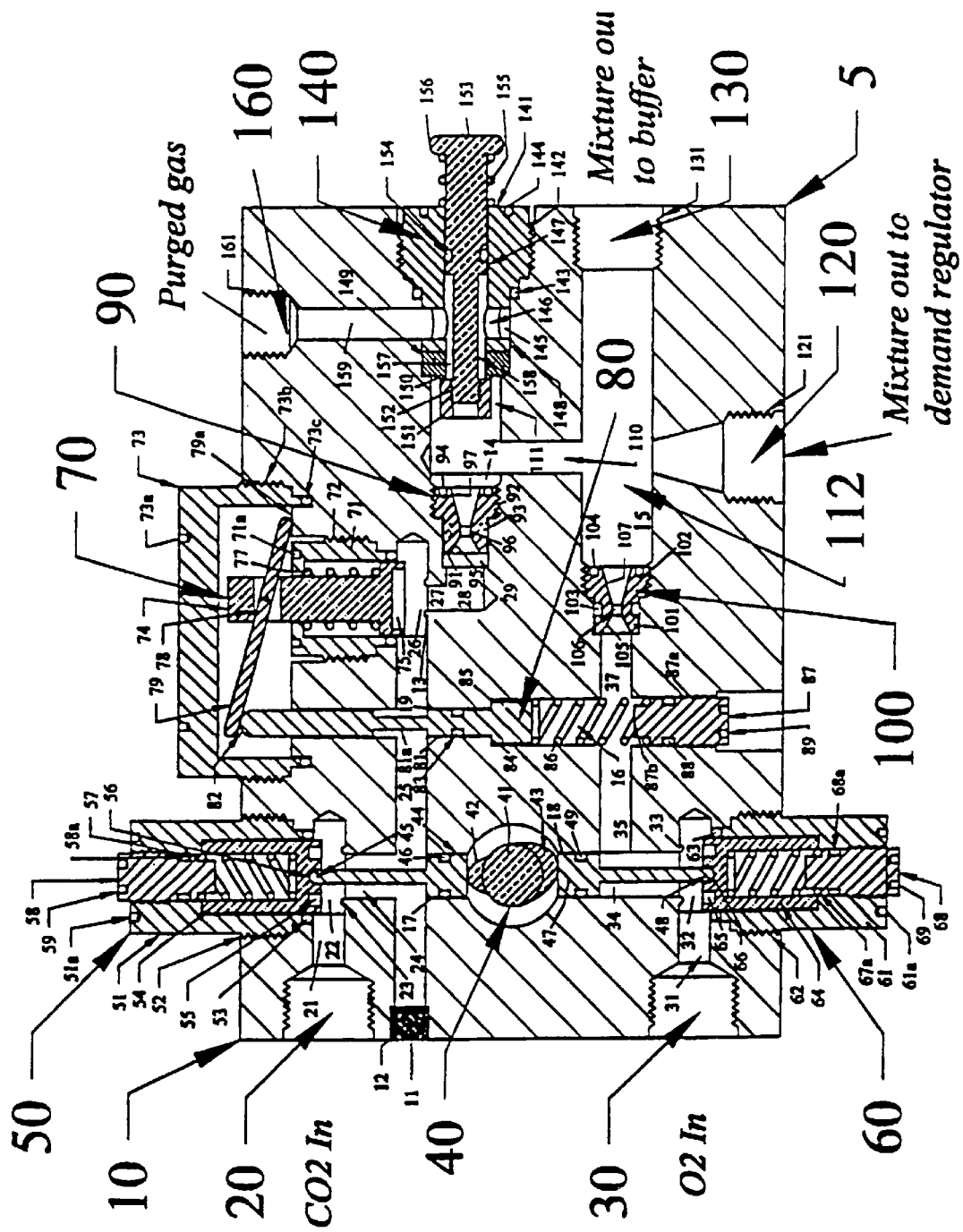
FIG. 2 is a detailed cross-sectional view of the first embodiment of the present invention.

The conduits may be any conduit compatible with safe medical delivery of carbon dioxide and oxygen. In one embodiment of the invention, the conduits include a connecting passage 21 or a flow passage 31 as shown in FIG. 2 The combining means may include a mixing chamber. For example, one embodiment of the invention includes a mixing chamber 110 as shown in FIG. 2. The invention also includes a means for administering the combined oxygen and carbon dioxide to the subject. The administering means may comprise a facemask including a conduit in fluid communication with the combining means, the face-mask adapted for placement over the face of the subject.

The apparatus preferably also includes a gas control means associated with the apparatus for controlling the pressure, flow rate and the ratio of the combined oxygen and carbon dioxide. The gas control means optionally includes a combination regulators (for example a regulator may be proximate to the oxygen or carbon dioxide source or the face mask) and sonic nozzles.

The apparatus optionally also includes a means for reducing the flow of carbon dioxide when the percentage of carbon dioxide in the combined carbon dioxide and oxygen exceeds about 6.5% by volume. In one variation, this means includes a carbon dioxide shut off valve 70. The reducing means optionally includes a shutoff member including on and off positions and an actuating means for actuating the shutoff member from the on position to the off position when the percentage of carbon dioxide in the combined carbon dioxide and oxygen exceeds about 6.5% by volume. The acutating means may include a sensor 80 shown in FIG. 2 having a piston means such as the body 81 and a biasing means such as the spring 86. Other devices for reducing or preventing carbon dioxide flow will be apparent.

According to the first embodiment, the invention preferably comprises a pneumatic control assembly for metering and mixing $O_2$ and $CO_2$ in prescribed proportions for applying the invented therapy. According to the second embodiment, the invention comprises a self contained apparatus, except for the $O_2$ supply, for administering the invented CO poisoning therapy.

Figure 1:
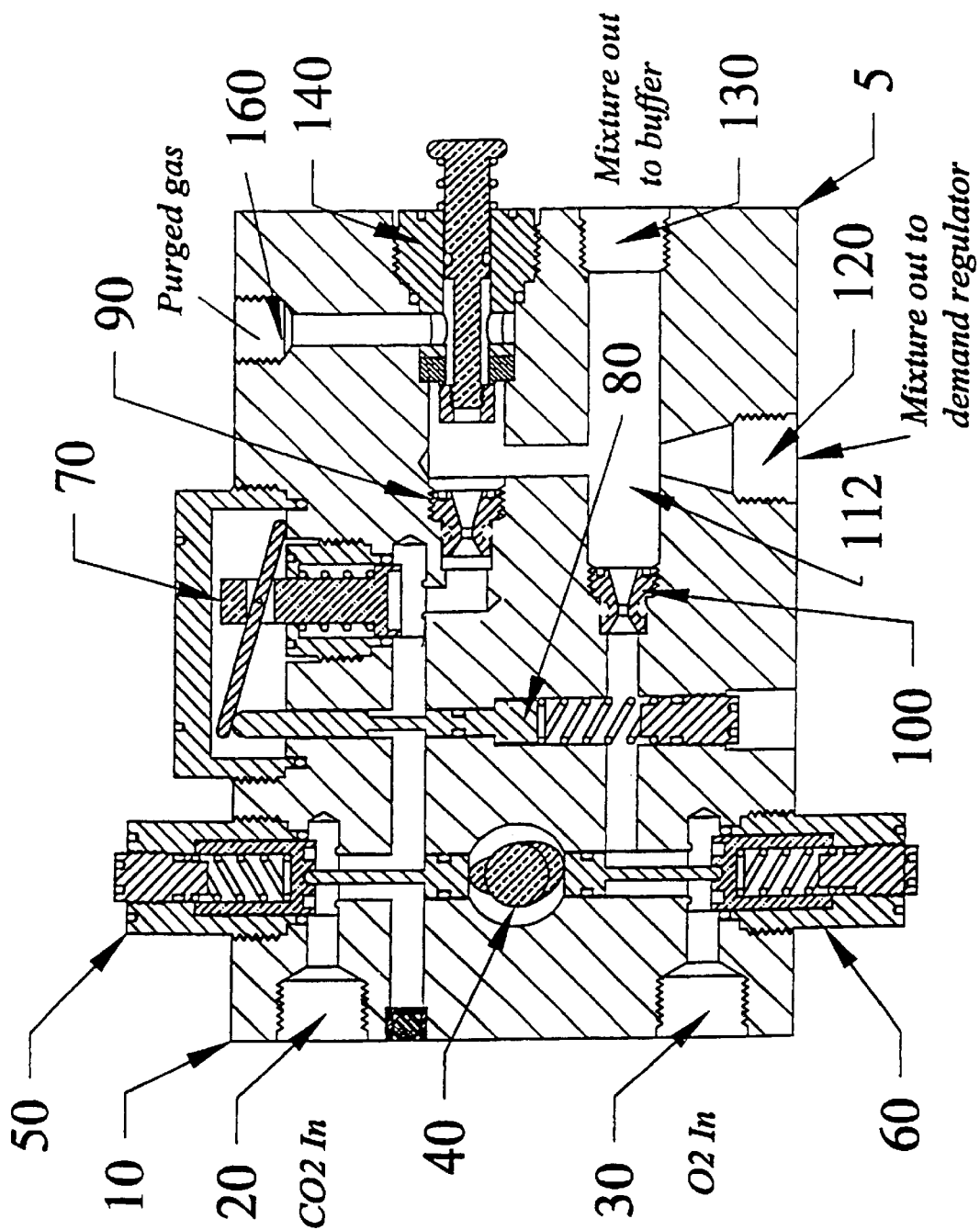
FIG. 1 is a general cross-sectional view of the first embodiment of the present invention.

Referring to FIG. 1, the pneumatic assembly 5 preferably consists of the following major components: body; gas selector; $CO_2$ valve; $O_2$ valve; $CO_2$ shut off valve; differential pressure sensor; $CO_2$ metering orifice; $O_2$ metering orifice; and purge valve. The pneumatic assembly S also consists of 5 ports: $CO_2$ inlet port; Oz inlet port; outlet to demand regulator and facemask; outlet to buffer volume; and purged gas outlet port. It will be apparent that parts of the embodiments of the invention can be omitted or varied.

The system receives pure $CO_2$ and $O_2$ at inlet ports 20 and 30 respectively. The pressures at ports 20 and 30 may be in the operating range of approximately 3.4 bar (50 psig). The inlet pressures for each gas are pre-set and relatively constant and are supplied from gas sources and pressure regulators not shown. Since the human body does not need precisely 5% $CO_2$, the pressures do not have to be exact. For example, if the input pressures fluctuated from 2.8 to 3.8 bar the mass flow rate would only vary by 11.4%, which is acceptable.

A rotary selection device 40 has two cam lobes to enable $O_2$ or $CO_2/O_2$ as required. Preferably, the apparatus has four positions, with positive detent stops for each selection. The positions are: OFF; MIXTURE: $O_2$ ; and OFF. The two off positions remind the operator to purge the system prior to selecting a gas flow position. As shown, in FIGS. 1 and 2 both gases are selected. Accordingly both the $CO_2$ valve 50 and the $O_2$ valve 60 are forced open by the cam lobes, enabling flow of both gases. If the $CO_2$ and $O_2$ pressures are nearly equal, differential pressure sensor 80 opens the $CO_2$ shutoff valve 70, allowing $CO_2$ to flow to the metering point. Should the $CO_2$ pressure significantly exceed the $O_2$ pressure, sensor 80 will retract and thereby shut-off valve 70 will close, and the flow of $CO_2$ will stop.

Metering orifices 90 and 100 meter the $CO_2$ and $O_2$ respectively in the correct proportions. Those orifices are preferably sonic. However, downstream backpressure may occasionally rise to the point where the orifices become sub-sonic. That brief condition is allowed since it represents low flow, or very shallow breathing on the patient's behalf. In this case the volumetric error of the gas mixture is quite low and the therapeutic value of the gas mixture is not appreciably diminished. The output of the two gases is combined in mixing chamber 110. The two gases collide at an angle to facilitate mixing, as for example 90°, as they enter mixing chamber 112, creating turbulence, and promoting mixing. The mixed gases pass on to outlet port 120, which is connected to a conventional demand type regulator and facemask (not shown). When the patient inhales, the demand regulator withdraws the inspiratory volume from the gas-mixture port 120. When the patient exhales, the demand regulator isolates the facemask from 120 and vents the expiratory gases to atmosphere. The system is assumed to store a quantity of the gas mixture in a buffer volume, to support large instantaneous demands. Outlet port 130 provides a connection between the buffer volume and the regulator port 120.

After usage, depressing purge valve 140 purges the system. That is, all gases stored in the apparatus and in the buffer volume are vented to port 160.

Figure 5:
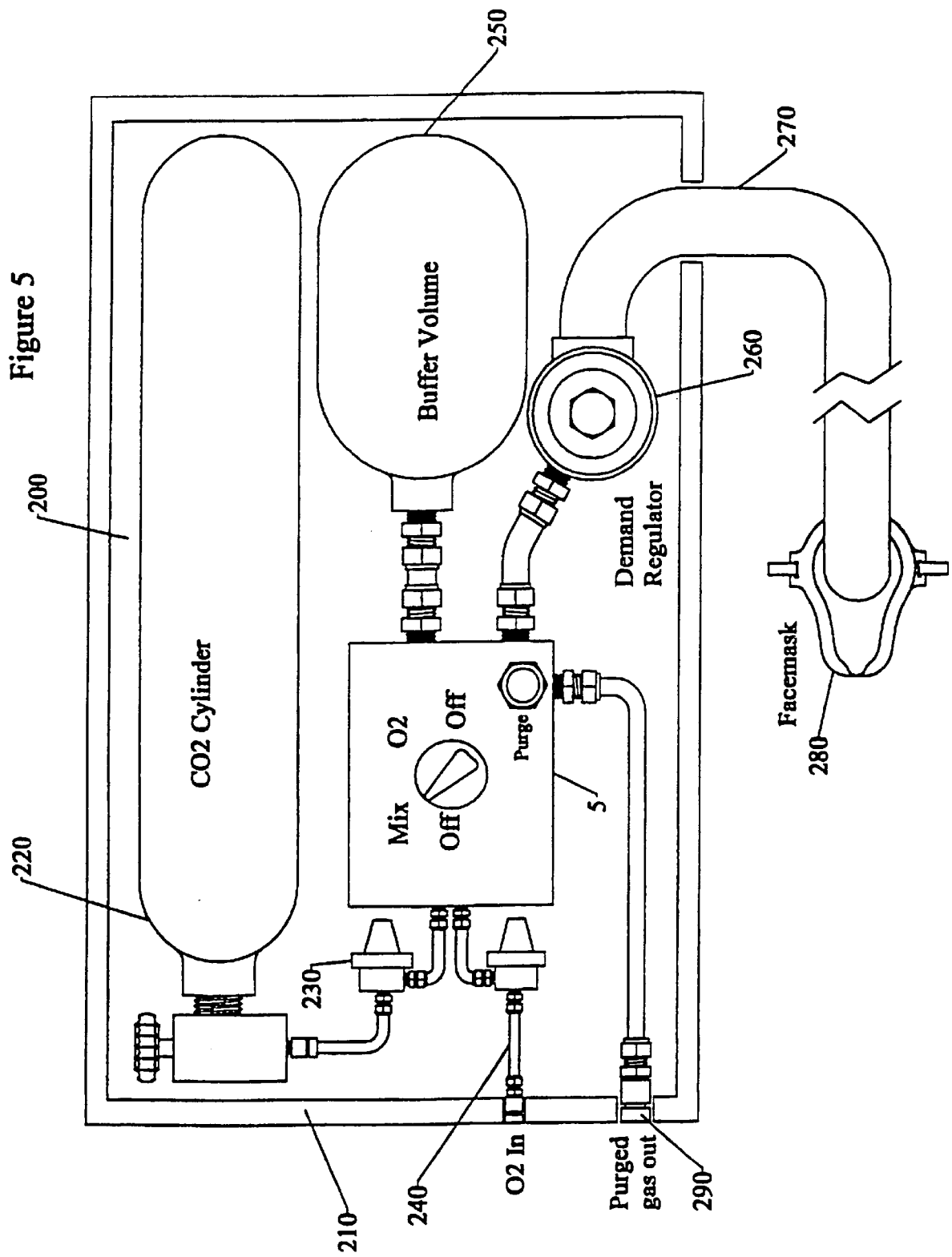
FIG. 5 is a general schematic diagram of the second embodiment of the present invention.

FIG. 5 shows a second embodiment of the invention 200, which includes the following major components: carry case 210; $CO_2$ supply 220; $CO_2$ regulator 230; $O_2$ regulator 240; control system 5; buffer volume 250; demand regulator 260; low pressure hose 270; face mask 280; purge line 290.

Preferably, the apparatus is enclosed in a portable case 210, to which all of the components would be mounted. This case is preferably the size of a briefcase. The apparatus includes a medium pressure storage system, for example a conventional cylinder 220 for storage of $CO_2$. Preferably the dimensions of the cylinder are 3" in diameter and 16" long. As the $CO_2$ stored pressures might in practice range between 3 and 100 bar, a metal or composite cylinder would preferably be used (such cylinders are commercially available). The stored $CO_2$ would be connected to a regulator 230, which reduces pressure to a low, relatively constant pressure (preferably about 3.4 bar). At extreme pressure, accuracy is not required, and a single stage unbalanced regulator would be acceptable (numerous such devices are commercially available). The regulated $CO_2$ would then be sealably connected to the pneumatic control device 5 described in the first embodiment above.

An $O_2$ input and regulation system 240 would receive unregulated $O_2$ from an external source via a quick disconnect. Preferably, the $O_2$ pressure would range from 3.4 to 160 bar. The received $O_2$ is connected to a regulator (part of 240) which reduces its pressure to a low, relatively constant pressure (typically 3.4 bar). At extreme pressure, accuracy is not required, and a single stage unbalanced regulator would be acceptable (numerous such devices are commercially available). The regulated $O_2$ would then be sealably connected to the pneumatic control device S described in the first embodiment above.

Depending on the selector position, control device 5 would then deliver no gas, pure $O_2$, or the invented therapeutic gas-mixture to both a cylindrical buffer volume 250 and to a demand regulator 260. The pressure in the buffer volume would normally swing between atmospheric pressure and approximately 20 psig, with its maximum pressure being the regulated pressures (approximately 3.4 bar). Accordingly, the buffer volume is preferably a low cost metal or plastic cylinder, fabricated from tubing (e.g. spherical ends are not required) preferably having dimensions of 4" in diameter and 8" long.

When the patient inhales, the demand regulator senses the sub-atmospheric pressure at its outlet port and opens its flow valve to restore a slightly positive pressure (about 1 to 1.5 kPa). Thus the inhalation event causes the demand regulator 260 to withdraw gas from the control system 5 and deliver that gas to the facemask 280. During inhalation, the demand regulator's valve throttles the flow to match the inspiratory volume demanded. Such demand regulators are commercially available When the patient stops inhaling, the pressure starts to rise above the 1 to 1.5 kPa set pressure and the demand regulator shuts off. A simple valve (preferably a rubber flapper or umbrella valve) in the outlet chamber 260 vents the outlet gases to atmosphere whenever an overpressure exists. Such an overpressure condition exists every time the patient exhales.

The outlet of the demand regulator 260 is connected to a conventional facemask 280 by preferably a flexible low-pressure hose 270. The items 260, 270, and 280 are readily available commercial parts.

FIG. 2 shows the control system 5 preferably housed in a non-sparking body 10, such as brass to prevent inadvertent problems in the presence of the $O_2$ gas. Regulated $CO_2$ (having a preferred inlet pressure of approximately 3.4 bar) is received at any suitable inlet port 20, such as a threaded female port. After entering port 20, the $CO_2$ would pass through a connecting passage 21 and enter valve chamber 22. If the $CO_2$ valve 50 is open (as shown), the $CO_2$ passes through the space between the valve seat 23 and the valve seal 55. If the valve 50 is shut (not shown), gas flow is prevented by seal 55 resting on seat 23. As shown, $CO_2$ flows through the annular space between throat area 24 and the actuator tip 45 and into interconnecting passage 25. Connecting passage 25 is permanently sealed after construction by a conventional ball 11 and plug 12 system.

$CO_2$ then passes through 25 (and around 81*a*) into valve chamber 26. If the $CO_2$ shutoff valve 70 is closed (not shown), seal 75 sitting on valve seat 13 blocks $CO_2$ flow. If valve 70 is open (not shown), the $CO_2$ passes through the space between the valve seat 13 and the valve seal 75. $CO_2$ then passes through the throat area 27 and into connecting passage 28. From passage 28 the gas turns an angle to facilitate mixing (for example about 90°) as it passes into orifice chamber 29. All of the flow passages (21, 25, 28), flow annuli (23-45, 27-81*a*), and valve-seat clearances (23-55,13-75) are chosen so as to be non-restrictive to flow when compared to the calibrated restriction presented by orifice insert 90.

Orifice insert 90 meters the $CO_2$ in accordance with the ideal gas law. The insert 90 is comprised of a body 91 with threaded section 92 for retaining the component in bore 14. An o-ring 93 (or other appropriate seal), seals the outside diameter of insert 90 to the inside diameter of cavity 29 so that all $CO_2$ flow must pass through the centre of orifice insert 90. The actual metering section of orifice insert 90 is comprised of a converging inlet section 95, a straight throat area 96 (which is the metering orifice) and a diverging pressure recovery section 97. Two holes 94 in the outlet face of orifice insert 90 allow the insert to be tightened by means of a special tool.

$CO_2$ exiting orifice insert 90 enters bore 14, then turns turns an angle such as to facilitate mixing (for example, about 90°) as it enters connecting passage 110. This angular turn creates turbulence, which helps to mix the $CO_2$ and $O_2$. Connecting passage 110 intersects mixing chamber 112, which is in direct communication with outlet port 120. Preferably port 120 is typically a female port, with threaded section 121, and is connected to a demand regulator. Gas in chamber 112 is also in communication with outlet port 130. Preferably, port 130 is typically a female port, with threaded section 131, and is connected to a buffer volume.

Regulated $O_2$ (having a preferred inlet pressure of approximately 3.4 bar) is received at any suitable inlet port 30, such as a threaded female port. After entering port 30, the $O_2$ would pass through a connecting passage 31 and enter valve chamber 32. If the $O_2$ valve 60 is open (as shown), the $O_2$ passes through the space between the valve seat 33 and the valve seal 65. If the valve 60 is shut (not shown), gas flow is prevented by seal 65 resting on seat 33. As shown, $O_2$ flows through the annular space between throat area 34 and the actuator tip 48 and into interconnecting passage 35.

$O_2$ then passes through 35 into valve chamber 16. The $O_2$ passes through the annular gap between chamber 16 and the "nose" 87b of adjuster 87 and on into orifice chamber 37. Some $O_2$ may also flow in the annular gap between 16 and spring 86. All of the flow passages (31, 35, 37), flow annuli (16-87b, 16-86), and valve-seat clearance (33-65) are chosen so as to be non-restrictive to flow when compared to the calibrated restriction presented by orifice insert 100.

Orifice insert 100 meters the $O_2$ in accordance with the ideal gas law. The insert 100 is comprised of a body 101 with threaded section 10, for retaining the component in bore 15. An o-ring 103 (or other appropriate seal), seals the outside diameter of insert 100 to the inside diameter of cavity 37 so that all $O_2$ flow must pass through the centre of orifice insert 100. The actual metering section of orifice insert 100 is comprised of a converging inlet section 105, a straight throat area 106 (which is the metering orifice) and a diverging pressure recovery section 107. Two holes 104 in the outlet face of orifice insert 100 allow the insert to be tightened by means of a special tool.

$O_2$ exits the orifice insert 100 and the mixing chamber 112, which is in direct communication with outlet port 120. During periods where the mass flow is entering the buffer volume, the $O_2$ gas stream continues straight through 112, and collides with the $CO_2$ gas stream at right angles, thus promoting mixing. The mixed gases then pass from 112 into port 130 for delivery to the buffer volume. During periods where the mass flow is passing to the demand regulator, the $O_2$ turns 90° in order to pass from mixing chamber 112 into outlet port 120. The turbulence from turning 90° and from the $O_2$ and $CO_2$ impinging one another at 90° promotes mixing. From 112, the mixed gas (or $O_2$ only if this operation is selected) enter port and is connected to a demand regulator.

The flow diameters seen by the metered and mixed gases (14, 15, 110, 112) are preferably sized so as to minimize pressure drop at high instantaneous flow rates. The nominal maximum inspiratory flow rate is assumed to 60 standard liters per minute.

Preferably, a rotary selector 40 is used to actuate $CO_2$ and $O_2$ valves 50 and 60. Selector 40 has two cam lobes, 42 and 43, which select $CO_2$ and $O_2$ respectively. The lobes are presumed to provide four positions: OFF; MIXTURE; $O_2$; and OFF. This arrangement always allows the user to select the other therapeutic gas stream (than that currently used) or OFF with one click of the selector. Additionally to move from one therapeutic gas stream to another requires two clicks of the selector as a reminder to the operator to purge the system prior to selecting the second therapeutic gas stream. Accordingly, the selector preferably includes a conventional ball-spring-detent system (not shown) so that the selector stops at each position. If the cam lobes are on a single plane (as shown), the selector would rotate through no more than 180°. If continuous 360° rotation were desired, the two cams would be placed on separate planes.

As shown in FIG. 2, cam lobe 42 has engaged $CO_2$ actuator 44 and moved it to its maximum open position. The actuator tip 45 engages a recess 56 in piston 54, lifting 54 off of valve seat 23. The end of tip 45 would typically be hemispherical and recess 56 would typically be conical or hemispherical so that the two parts would move freely and smoothly. Actuator 44 slides in bore 17 preferably machined into body 19, and is sealed to that bore by o-ring 46 (or other appropriate seal). The height of the cam lobe 42, from the base circle of 41 would typically be such a fraction of sealing diameter of seat 23 such as to ensure that the valve seal 55 does not impact the flow rate when piston 54 is in its open position, for example about 40%. Piston 54 rides in a companion bore in body 51, with suitable radial clearance. Spring 57 acts to move piston 54 to its closed position when cam lobe 42 is not selecting $CO_2$. In that case, the force from spring 57 must overcome the friction from o-ring 46 and provide the force needed to create an effective seal between SS and 23. As shown, adjuster 58, sealed by o-ring S8a to body SI, is available to set the pre-load from spring 57. A special tool engaging the two holes S9 in its face turns adjuster 58. The valve body 5.1 is retained in body 10 by thread 52, and sealed from external leakage by o-ring 53. A special tool engaging the two holes 51a in its face tightens the valve body 51.

As shown in FIG. 2, cam lobe 43 has engaged $O_2$ actuator 47 and moved to its maximum open position. The actuator tip 48 engages a recess 66 in piston 64, lifting 64 off of valve seat 33. The end of tip 48 is preferably hemispherical and recess 66 is preferably conical or hemispherical so that the two parts move freely and smoothly. Actuator 47 slides in bore 18 preferably machined into body 10, and is sealed to that bore by o-ring 49 (or other appropriate seal). The height of the cam lobe 43, from the base circle of 41 is preferably at least 40% of sealing diameter of seat 33. That value ensures that the valve seal 65 does not impact the flow rate when piston 64 is in its open position. Piston 64 rides in a companion bore in body 61, with suitable radial clearance. Spring 67 acts to move piston 64 to its closed position when cam lobe 43 is not selecting $O_2$ —In that case, the force from spring 67 must overcome the friction form o-ring 49 and provide the force needed to create an effective seal between 65 and 33. As shown, adjuster 68, sealed by o-ring 68a (or other appropriate seal) to body 61, is available to set the pre-load from spring 67. A special tool engaging the two holes 69 in its face turns adjuster 68. The valve body 61 is retained in body 10 by thread 62, and sealed from external leakage by o-ring 63(or other appropriate seal). A special tool engaging the two holes 61a in its face tightens the valve body 61.

Referring to FIG. 2, sensor 80 is comprised of body 81 which slides in bore 19 machined into body 10, and is sealed to that bore by o-ring 83 (or other appropriate seal). The 35 outer diameter of body 81 is reduced in area Sla so as to minimize the flow restriction in connecting passage 25. Sensor tip 82 operates against lever 79, which moves through an arc to raise piston 74 off of valve seat 13. Specifically, the right end of lever 79 rests against the bottom ledge of groove 79a, which is in body 10, and acts as a pivot point for 79. Lever 79 passes through slot 78 in piston 74, with the 78-74 contact point serving to raise or lower 74. The end of tip 82 is preferably hemispherical so that lever 79 will move freely and smoothly. When the pressures in chambers 16 and 27 ($O_2$ and $CO_2$) are roughly equal, spring 86 acts to move sensor 81 to its fully open position, moving piston 74 off of seat 13, and enabling $CO_2$ to flow. Adjusting the pre-load on spring 86 by turning adjuster 87 largely sets the $CO_2$—$O_2$ differential pressure required to close sensor 80. Adjuster 87 slides in bore 16 and is sealed to that bore by o-ring 88 (or other appropriate seal). A special tool engaging the two holes 89 in its face preferably tightens the adjuster 87. Its position is retained by thread 87a. The fully open position of sensor 80 is controlled by lip 84 on body 81 engaging a seat 85 machined in the end of bore 16.

The fully open position of sensor 81 preferably provides a gap (13-75) such as to ensure that the valve seal does not impact the flow rate when piston 74 is in its open position, as for example, at least 40% of the sealing diameter of seat 13. Piston 74 rides in a companion bore in body 71, with suitable radial clearance. Spring 77 acts to move piston 74 to its closed position when sensor 81 retracts to disable $CO_2$ flow.

The mixed gas in chamber 112 is communicated to the input of purge valve 140 by passage 111. Valve 140 includes a plunger 153 attached to seat 151 by thread 152. Seat 151 is normally closed against the protruding seal profile 150 of elastomeric seal 149 (or other suitable sealing material), preventing the flow of gases into the purge port 161. This normally closed state is maintained by spring 155 acting against purge body 141 and pushbutton 156, to maintain a closing force on the 150-151 seal interface. Plunger 153 slides in bore 147 of body 141 and is sealed to that bore by o-ring 154 (or other suitable sealing means). Body 141 is retained in body 10 by thread 142 and sealed from external leakage by o-ring 143 (or other suitable sealing means). Body 141 is preferably tightened by a special tool, which engages the two holes 144 on the rear face of 141. When pushbutton 156 is depressed, seat 151 moves away from seal 150 admitting purge gas into the annular space between throat 157 and plunger pin 158. The purge gas then passes into the annular space between bore 147 and pin 158. The outside diameter of body 141 has an annular relief 145, which is intersected by four through holes 146. The 145-146 system allows purge gas in the 147-158 cavity to pass first into connecting chamber 159 and then into the purge port 160. Port 160 is typically a female port with thread 161.

Figure 6:
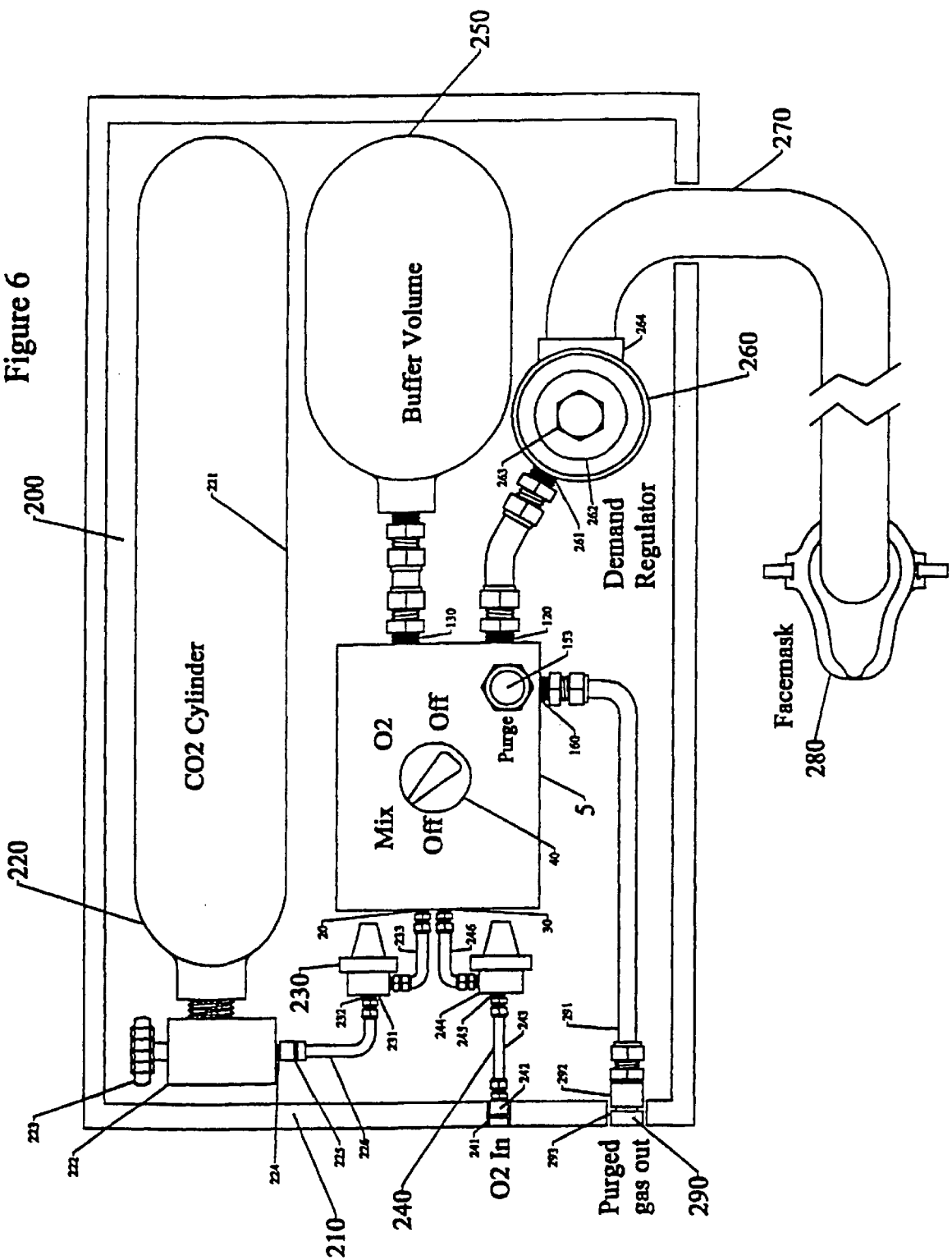
FIG. 6 is a detailed schematic diagram of the second embodiment of the present invention.

As shown in FIG. 6, a briefcase-sized system 200 would include all of the items needed to provide the therapeutic gas mixture, except for $O_2$ storage. As ambulances, emergency vehicles, fire trucks and hospitals, or other health institutions, already have $O_2$ storage available, there is no benefit to including the $O_2$ storage system in such a device.

The apparatus preferably includes a suitcase type of enclosure 210, which would house and mount all of the equipment. The largest item is most likely the $CO_2$ storage system 220. System 220 preferably includes a $CO_2$ source 221, capable of operating at least 100 bar. The outlet of 221 accommodates a cylinder valve 222, with a manual shut-off valve 223 for switching $CO_2$ sources, an outlet port 224, and a quick connect 225. Quick connect 225 would be permanently attached to a line 226, which delivers the unregulated $CO_2$ to the pressure regulator 230. Preferably, a full $CO_2$ cylinder would preferably contain enough $CO_2$ to handle two therapy events of 30 minutes each, at 60 liters per minute inspiratory flow at 5% $CO_2$ by volume. The $CO_2$ cylinders 221 would be replaced routinely (and after each use) and re-filled as an unrelated activity.

The $CO_2$ regulator 230 includes an inlet 232, a main regulator section 231, and an outlet 233. The regulating section 231 preferably comprises a single stage, non-balanced conventional pressure regulator. The output of the regulator would be permanently connected to the inlet port 20 of control device 5 (previously described).

The $O_2$ is preferably sourced externally. The $O_2$ circuit 240 includes a portal 241 in the suitcase 210 through which a quick-connect 242 passes. Quick connect 242 is connected to line 243 which routes the input $O_2$ to pressure regulator 244. The $O_2$ regulator 244 includes an inlet 245 and an outlet 246. The regulating section 244 preferably comprises a single stage, non-balanced pressure regulator. Commercial devices are readily available. The output of the regulator is permanently connected to the inlet port 30 of control device 5 (previously described).

Control device 5 includes a selector 40, to choose $O_2$, Mixture, or no gases. A button 153 would be used to purge the system after use, with purge gases being vented to port 160. Purged gases would be plumbed through line 291 to a terminal vent fitting (or quick connect) 292, passing through a portal 293 in the carrying case.

The gas output of control device 5 would appear at ports 120 and 130. Port 130 would be permanently connected to a buffer volume 250. As buffer 250 typically sees only 20 psig, it would preferably be of inexpensive construction, such as from thin wall metal pipe with simple end caps. Preferably, the dimensions of the buffer volume are 4" diameter by 8" in length.

Port 120 is connected to a demand-type regulator 260 (previously described). At a minimum, regulator 260 would include an inlet 261, a main regulator section 262, an over pressure relief valve 263, and an outlet 264. Regulator 260 is connected to a conventional facemask 280 by a conventional flexible hose 270.

Figure 3:
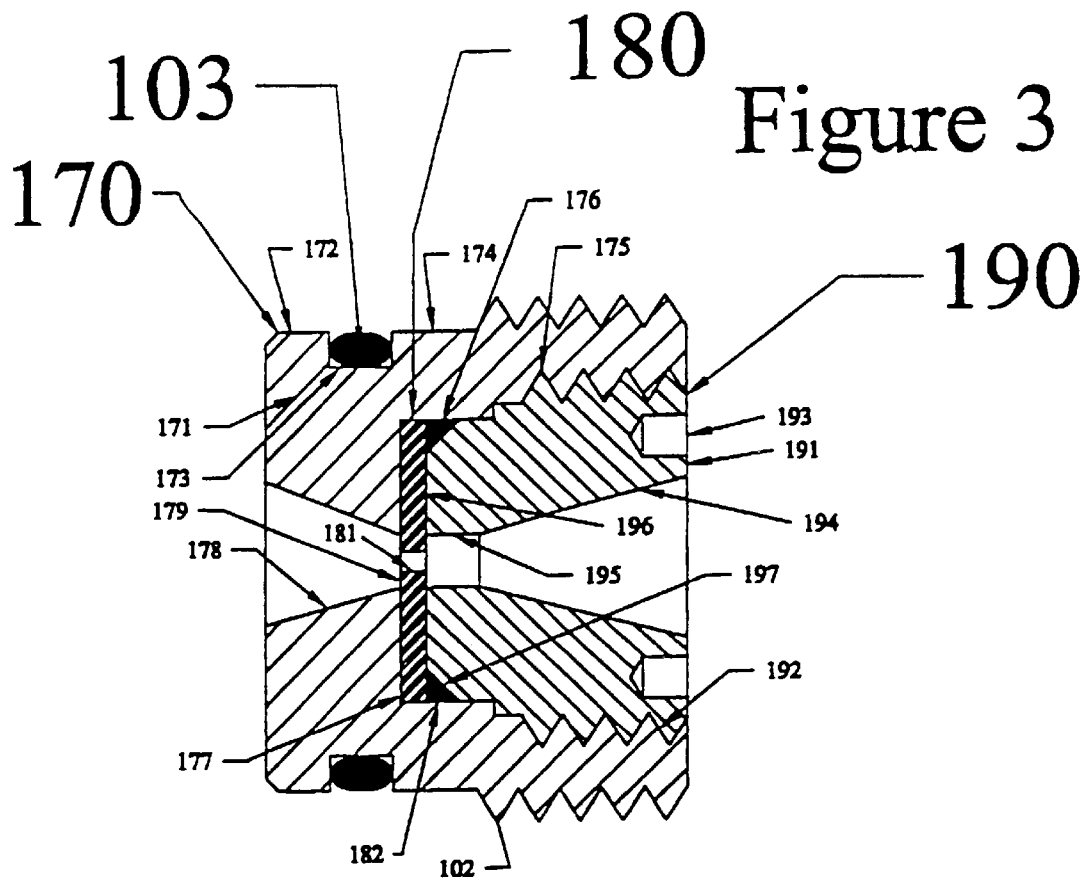
FIG. 3 is a cross-sectional view of an alternative orifice arrangement.

For example, FIG. 3 shows an alternative orifice arrangement. Certain combinations of design criteria (buffer volume, $CO_2$ and $O_2$ pressure, and maximum and minimum respiratory rates) can require very small orifice sizes. In such cases, the design format shown for orifices 90 and 100 may be impractical to machine. For example, orifice size could be as small as 0.003", which is very difficult to mechanically machine using conventional methods. Accordingly, an alternative orifice arrangement is provided, as shown in FIG. 3, orifice insert 170 includes an outer body 171, machined conventionally. Body 171 has a similar o-ring sealing diameter 171, and the same o-ring (203) as inserts 90 and 100. Body 171 includes a conventional o-ring gland 173. A similar body outside diameter 174 would be used, along with the same thread $10_2$, as seen in 90 and 100. Body 171 includes a converging inlet section 178, terminating at face 177, with a relatively large terminal outside diameter 179. A preferably thin, circular, flat orifice plate 180 would be inserted from the rear of body 171 and is seated against the face 177. The orifice plate preferably comprises metal substrate with a small through hole 181. Electron discharge machining, laser drilling, mechanical micro machining, and chemical micro-machining means can reliably produce such small holes. The hole 181 would be the actual metering orifice, and the thickness of the plate 180 would provide the desired throat depth. Plate 180 is held in body 171 by a plug 190. Plug 190 threads into 171 via thread 192, and would seal to 180 and 171 by seal 182. Plug 190 creates a chamfer type o-ring gland via surface 197 and sits against the orifice with surface 196. Where practical, plug 190 may preferably have a second throat section 195 and a diverging pressure recovery section 194. Plug 190 is preferably tightened into body 171 via a special tool engaging two holes 193 in its rear face. A commercially available thread sealant would lock plug 190 to orifice insert 170 so that it would function as an integral piece and could be installed and removed from body 10 without the two pieces separating.

Figure 4:
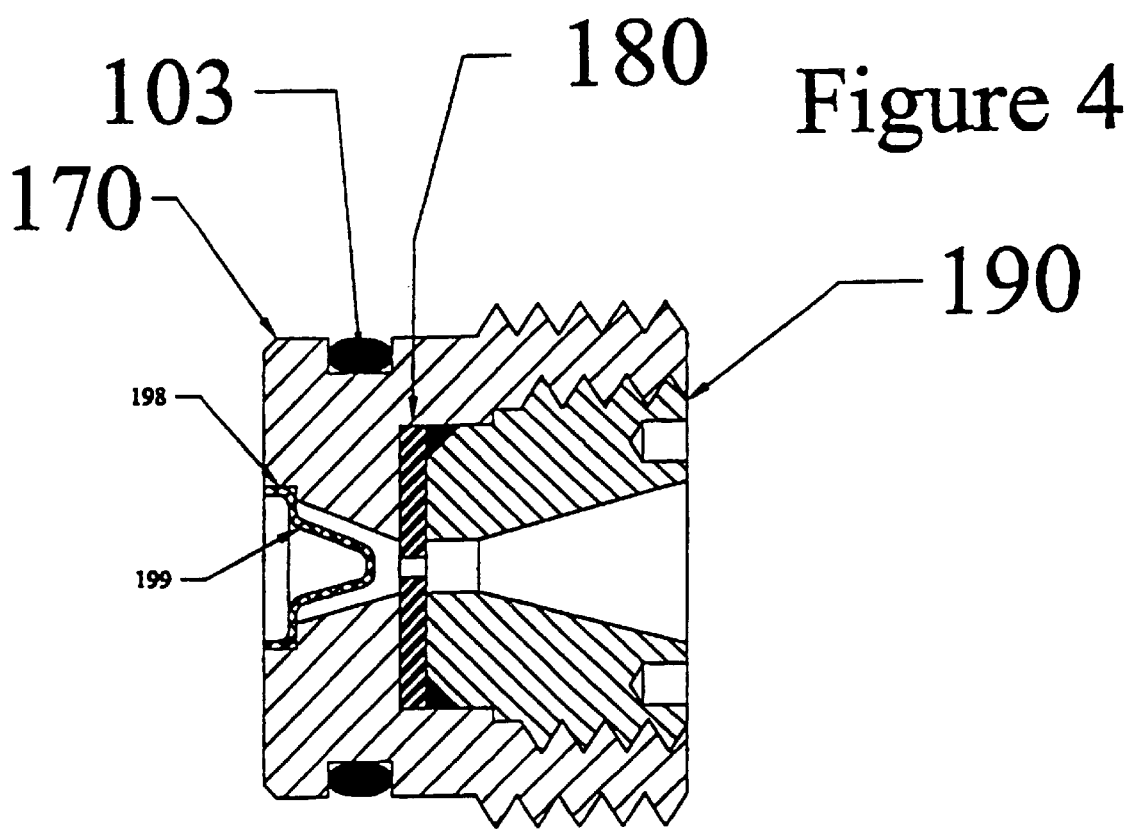
FIG. 4 is a cross-sectional view of a filtering assembly.

A filtration means is optionally provided to keep the orifices clean. In the case of very small orifices, there could be a concern about foreign particles lodging in and blocking the metering orifices. In such a case, a filter element could be included in each orifice. As shown in FIG. 4, filter element 199 could be press fitted into a recess 198 in insert 170. Such filter elements are commercially available and could include a wire screen, a sintered (porous) brass or porous fabric.

It will be appreciated that the above description relates to the preferred embodiments by way of example only. Many variations on the apparatus for delivering the invention will be obvious to those knowledgeable in the field, and such obvious variations are within the scope of the invention as described and claimed, whether or not expressly described.

All patents, patent applications (including Canadian application no. 2,269,890), and publications referred to in this paper are incorporated by reference in their entirety.

What is claimed is:

1. An apparatus for treating carbon monoxide poisoning in a subject by administering to the subject oxygen from a source of oxygen and carbon dioxide from a source of carbon dioxide, comprising:

an oxygen conduit defining an oxygen inlet and an oxygen outlet, the oxygen inlet adapted for fluid communication with the source of oxygen;

a carbon dioxide conduit defining a carbon dioxide inlet and a carbon dioxide outlet, the carbon dioxide inlet adapted for fluid communication with the source of carbon dioxide;

a means for combining the oxygen and the carbon dioxide, the means of combining being disposed downstream from the oxygen outlet and the carbon dioxide outlet;

a means for administering the combined oxygen and carbon dioxide to the subject;

means for controlling the pressure, flow rate and the ratio of the combined oxygen and carbon dioxide, comprising an oxygen regulator for controlling oxygen pressure located between the oxygen source and the means for combining the oxygen and the carbon dioxide, a carbon dioxide regulator for controlling carbon dioxide pressure located between the carbon dioxide source and the means for combining the oxygen and the carbon dioxide;

an oxygen sonic nozzle downstream of the oxygen regulator for dispensing the oxygen; and a carbon dioxide sonic nozzle downstream of the carbon dioxide regulator dispensing the carbon dioxide.

2. The apparatus of claim 1, wherein the apparatus further comprised a buffer in fluid communication with the means for combining, the buffer including combined oxygen and carbon dioxide.

3. A portable kit for treating carbon monoxide poisoning, comprising the apparatus of claim 1.

4. A method of treating carbon monoxide poisoning, comprising administering to a subject an effective amount of combined oxygen and carbon dioxide from the apparatus of claim 1.

5. The apparatus of claim 1, wherein the oxygen and sonic nozzles dispense the oxygen and the carbon dioxide, respectively, according to a predetermined flow rate.

6. The apparatus of claim 1, further comprising a means for reducing a flow of the carbon dioxide when a percentage of carbon dioxide in the combined carbon dioxide and oxygen exceeds about 6.5% by volume.

7. The apparatus of claim 6, wherein the reducing means prevents the flow of carbon dioxide.

8. The apparatus of claim 6, wherein the means for reducing the flow of the carbon dioxide comprises a differential pressure sensor downstream of at least one of the carbon dioxide source and the oxygen source.

9. The apparatus of claim 1, wherein the means for reducing is located proximate to the conduits and is in fluid communication with the oxygen and the carbon dioxide sources.

10. The apparatus of claim 6, wherein the means for reducing means comprises:

a shutoff member located proximate to the carbon dioxide conduit having an on position in which the shutoff member permits the carbon dioxide to communicate from the carbon dioxide source to the means for combining and an off position in which the shutoff member prevents the carbon dioxide from communicating from the carbon dioxide source to the combining means;

a means for actuating the shutoff member from the on position to the off position when the percentage of carbon dioxide in the combined carbon dioxide and oxygen exceeds about 6.5% by volume, the means for actuating operably connected to the shutoff member and responsive to differential pressure in the oxygen conduit and the carbon dioxide conduit.

11. The apparatus of claim 10, wherein the means for actuating comprises:

a piston in fluid communication with the oxygen conduit, the piston located proximate to the oxygen conduit and including a first position in which the piston means is biased away from the oxygen conduit and actuates the shutoff member to the on position and actuated the shutoff member to the on position and a second position in which the piston is biased towards the oxygen conduit and actuates the shutoff member to the off position;

a means for biasing for urging the piston toward the second position;

the piston normally being biased by oxygen towards the first position against a force of the means for biasing means, the piston being urged toward the second position by the biasing means when oxygen pressure decreases in the oxygen conduit.

12. The apparatus of claim 1, wherein the combining means comprises a mixing chamber.

13. The apparatus of claim 1, wherein the means for administering comprises a face-mask including a conduit in fluid communication with the means for combining, the face-mask adapted for placement over a portion of the subject.

14. The apparatus of claim 13, wherein the face-mask further comprises a pressure regulator.

15. The apparatus of claim 1, wherein the means for administering is adapted to administer the combined oxygen and carbon dioxide to the subject in an amount effective to increase the breathing rate of the subject.

16. The apparatus of claim 15, wherein the carbon dioxide is between about 3.5 percent to about 6.5 percent by volume of the combined oxygen and carbon dioxide.

17. The apparatus of claim 15, wherein the combined carbon dioxide and oxygen are in a ratio of about 19:1 by volume.

18. The apparatus of claim 15, wherein the combined carbon dioxide and oxygen have a pressure of between about 1 atm to about 20 psig.

19. The apparatus of claims 1, wherein the oxygen and the carbon dioxide conduits are connected to a tubular housing and extend into the housing.

20. The apparatus of claim 19, wherein the oxygen and the carbon dioxide conduits are defined by the housing.

21. The apparatus of claim 20, wherein the oxygen and the carbon dioxide conduits are integrally defined by the housing.

22. The apparatus of claim 21, wherein the apparatus is configured so as to be portable.

23. The apparatus of claim 22, further comprising a carbon dioxide tank adapted to be connected to the carbon dioxide conduit.

24. The apparatus of claim 23, wherein the apparatus is configured so as to fit in a briefcase.

25. The apparatus of claim 24, wherein the subject comprises a human.

26. The apparatus of claim 25, wherein the apparatus is operable without electric power.

* * * * *